United States Patent [19]
Mavretic

[11] Patent Number: 6,046,594
[45] Date of Patent: Apr. 4, 2000

[54] METHOD AND APPARATUS FOR MONITORING PARAMETERS OF AN RF POWERED LOAD IN THE PRESENCE OF HARMONICS

[75] Inventor: Anton Mavretic, Marlton, N.J.

[73] Assignee: Advanced Energy Voorhees, Inc., Voorhees, N.J.

[21] Appl. No.: 08/798,881

[22] Filed: Feb. 11, 1997

[51] Int. Cl.$^7$ .................................................. G01N 27/62
[52] U.S. Cl. ...................... 324/520; 324/76.29; 324/646; 324/619; 343/735
[58] Field of Search .................................. 324/619, 639, 324/646, 623, 620, 520, 616, 709, 76.29; 343/735

[56] References Cited

U.S. PATENT DOCUMENTS

| | | | |
|---|---|---|---|
| 5,343,404 | 8/1994 | Girgis | 364/484 |
| 5,691,642 | 11/1997 | Dobkin | 324/464 |
| 5,861,752 | 1/1999 | Klick | 324/464 |

OTHER PUBLICATIONS

Advanced Energy Industries, Inc.,"13.56–MHZ RFz 60 Plasma Impedance Probe", 8 pages No date.
Advanced Energy Industries, Inc., "An Intelligent Solution to RF Load–Power Variability", vol. 2, No. 3, 3rd Quarter, 1995, 8 pages.
Michael Klick, "Nonlinearity of the radio–Frequency Sheath", J. Appl. Phys. 79 (7), Apr. 1, 1996, 6 pages.
University of Minnesota, "12th International Symposium on Plasma Chemistry Proceedings vol. 1", Aug. 1995, 5 pages.
Adolf–Slaby–Institut, "European Semiconductor", 4 pages No date.
Adolf–Slaby–Institut, "Plasma Monitoring by Hercules", 8 pages No date.
Fourth State Technology, Inc., "Chamber Matching with the RFMS: A Case Study", 17 pages No date.
Fourth State Technology, Inc., "The How–To's of RF Metrology", 9 pages No date.
Fourth State Technology, Inc., "RF Metrology Baseline Study–LRC 4500", 9 pages No date.
Fourth State Technology, Inc., "Enhancing Equipment Performance: Applied Materials 5000 PECVD", 10 pages No date.
Fourth State Technology, Inc., "Enhancing Equipment Performance: Novellus Concept One", 8 pages No date.
Fourth State Technology, Inc., "Enhanced Process Control for the LRC 4720", 5 pages No date.

*Primary Examiner*—Josie Ballato
*Assistant Examiner*—Jose M. Solis
*Attorney, Agent, or Firm*—Blakely Sokoloff Taylor & Zafman, LLP

[57] ABSTRACT

A method and apparatus for measuring electrical characteristics (e.g. current, voltage, phase, etc.) between a power source and a load at a set of harmonic frequencies to determine information about the load (e.g., load impedance, power dissipation, etc). According to one aspect of the invention, a first circuit detects a set of electrical characteristics (e.g., current, voltage, and/or phase) of a signal between the power source and the load. A second circuit, coupled to the first circuit to receive the set of electrical characteristics, provides data representing the set of electrical characteristics at a harmonic frequency associated with the signal. A third circuit, coupled to the second circuit, receives the data and determines information about the load (e.g., impedance, power dissipation, discharge current, etc.) at the harmonic frequency. The information could be used in any number of ways, such as controlling an impedance matching network that may be used in conjunction with the power source and the load, identifying/monitoring a load condition(s), etc.

25 Claims, 3 Drawing Sheets

METHOD AND APPARATUS FOR MONITORING PARAMETERS OF AN RF POWERED LOAD IN THE PRESENCE OF HARMONICS

BACKGROUND OF THE INVENTION

1. Field of the Invention

The present invention relates to the field of data collection devices. In particular, the present invention relates to a method and apparatus for measuring electrical characteristics (e.g., current, voltage, phase, etc.) between a radio frequency (RF) power source and a load at a set of harmonic frequencies to determine information about the load (e.g., load impedance, power dissipation, etc).

2. Background Information

In many applications in which a load is powered by an RF signal provided by a source, it is useful, and sometimes necessary, to determine certain load parameters (e.g., load impedance, power dissipation, etc). For example, devices such as impedance matching networks in RF powered systems generally attempt to accurately detect voltage, current, power, and/or phase in the RF powered system to match impedance between an RF power source and a load, and thereby provide maximum power transfer to the load. An impedance matching network is often necessary, for example, in an RF powered plasma processing system utilizing an RF power generator (source) and a plasma chamber (load) to ensure that a desired power delivery level is matched and maintained for the plasma chamber.

Unfortunately, in some applications, monitoring load parameters with desired accuracy may be relatively difficult. Nonlinear voltage-current relationships of some types of loads and variable frequency of a power signal provided by a power source can make determining load parameters relatively difficult. In the case of RF powered plasma processing systems, for example, the dynamic impedance of the plasma chamber may produce harmonics, which, in turn, can return from an input of the plasma chamber to produce relatively substantial errors in diagnostics/measuring devices and/or impedance matching networks. In particular, the plasma chamber may produce harmonics as its impedance changes and stray current is discharged due to such factors as plasma chamber pressure, temperature, chemical composition, plasma ignition, chamber dimension, etc. Without taking harmonics into consideration, information about a load (e.g., a plasma chamber) may be incomplete and/or inaccurate.

In some applications, relatively complete and accurate information regarding an RF powered load is desired. For example, in the case of RF powered plasma processing systems, information about the plasma chamber, such as impedance and/or power transfer at fundamental and harmonic frequencies, enables impedance matching networks to operate optimally. Furthermore, characteristics of the plasma chamber at various harmonics could be used as "fingerprints" to allow identification/repetition of particular plasma processes.

In the past, data collection devices for applications such as RF powered plasma processing systems have not been able to provide desired accuracy in the presence of harmonics or have been relatively expensive and difficult to implement. For example, some prior art data collection devices collect data directly from a plasma chamber by using a measuring probe that is inserted into the plasma chamber or is part of a wall of the plasma chamber. However, such prior art data collection devices are intrusive (i.e., they may affect plasma chamber conditions), and thus, relatively difficult to implement in some instances since the probe must be directly inserted into the plasma chamber. Furthermore, such prior art data collection devices are relatively expensive since they generally must utilize relatively complex measuring probes inside the plasma chamber to detect chemical properties and perform relatively complex calculations to determine information about the plasma chamber. Other prior art data collection devices are not capable of measuring impedance/power dissipation of a load at harmonic frequencies.

Therefore, what is desired is a relatively inexpensive, transparent (in situ) system for interfacing with any number of RF powered systems for determining information about an RF powered load (e.g., load impedance, power dissipation, etc.) even in the presence of harmonics.

SUMMARY OF THE INVENTION

The present invention relates to the field of data collection devices. In particular, the present invention relates to a method and apparatus for measuring electrical characteristics (e.g. current, voltage, phase, etc.) between a power source and a load at a set of harmonic frequencies to determine information about the load (e.g., load impedance, power dissipation, etc). According to one aspect of the invention, a first circuit detects a set of electrical characteristics (e.g., current, voltage, and/or phase) of a signal between the power source and the load. A second circuit, coupled to the first circuit to receive the set of electrical characteristics, provides data representing the set of electrical characteristics at a harmonic frequency associated with the signal. A third circuit, coupled to the second circuit, receives the data and determines information about the load (e.g., impedance, power dissipation, discharge current, etc.) at the harmonic frequency. The information could be used in any number of ways, such as controlling an impedance matching network that may be used in conjunction with the power source and the load, identifying/monitoring a load condition(s), etc.

BRIEF DESCRIPTION OF THE DRAWINGS

The invention is illustrated by way of example and not limitation in the following Figures. In the drawings.

DETAILED DESCRIPTION

Described is a method and apparatus for measuring electrical characteristics (e.g. current, voltage, phase, etc.) between a power source and a load at a set of harmonic frequencies to determine information about the load (e.g., load impedance, power dissipation, etc). In the following description, numerous specific details are set forth to provide a thorough understanding of the invention. However, it is understood that the invention may be practiced without these specific details. In other instances, well-known circuits, structures and techniques have not been shown in detail in order not to obscure the invention.

OVERVIEW OF AN EMBODIMENT OF THE INVENTION

Figure 1:
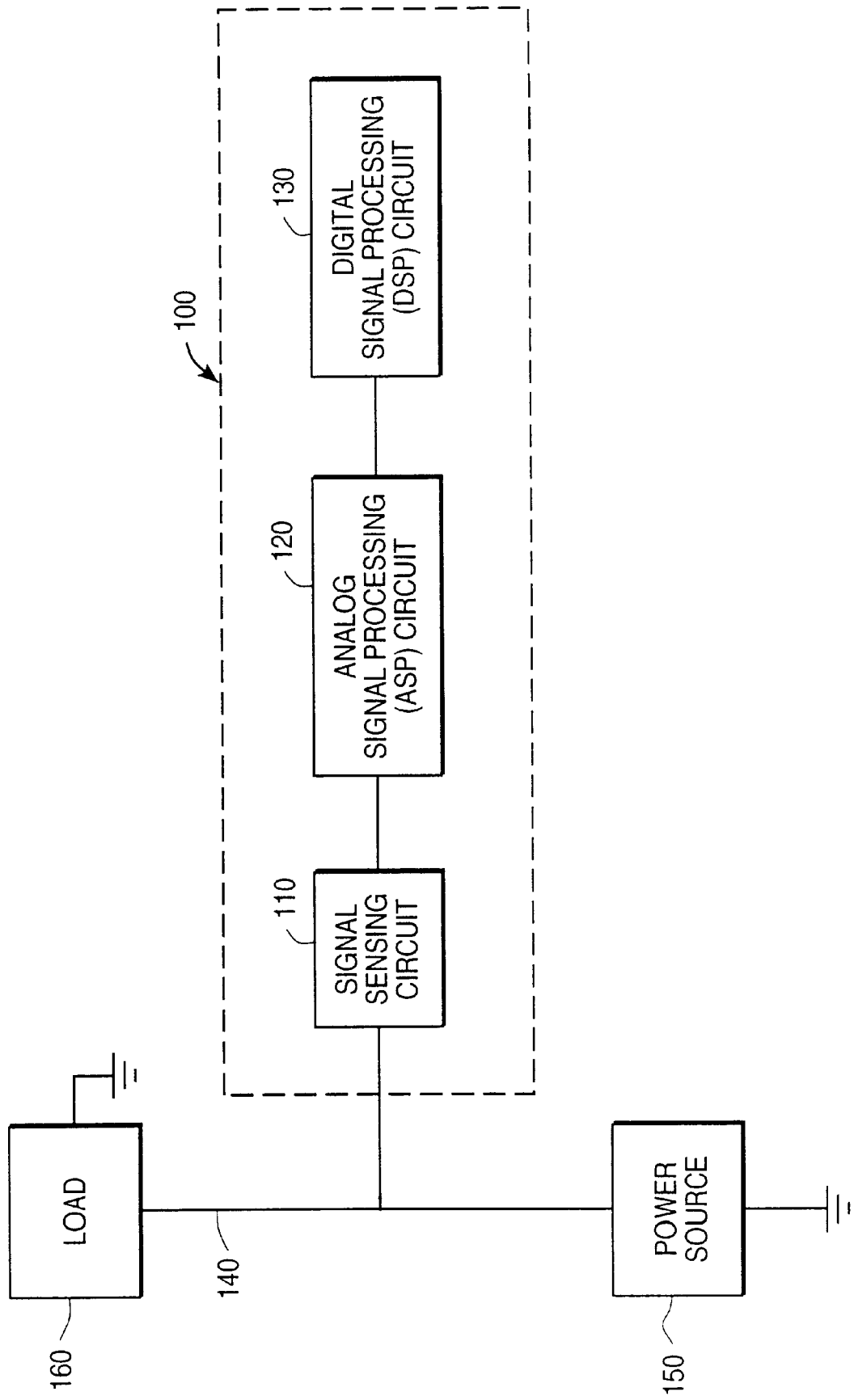
FIG. 1 is a block diagram of a system in which one embodiment of the invention can be utilized.

FIG. 1 is a block diagram of a system in which one embodiment of the invention can be utilized. A system 100 is shown which can be used to detect and analyze signals and associated harmonics in a system comprising a power source 150 coupled to a load 160 via a transmission line 140. In the described embodiment, the power source 150 provides a (power) signal to the load 160 via the transmission line 140.

The system 100 comprises a signal sensing circuit 110 that samples the signal present on the transmission line 140 and detects a set of electrical characteristics of the signal, such as current, voltage, and the phase difference between the current and the voltage associated with the signal. It should be appreciated that the signal sampled by the signal sensing network can be incident to or reflected from the load 160.

Coupled to the signal sensing circuit 110 is an analog signal processing (ASP) circuit 120. As described in further detail below with reference to FIG. 3, the ASP circuit 120 may include any combination of a wave shaping network, an amplifier network, a filtering network, an AC/DC converter, an analog-to-digital converter, etc. The ASP circuit 120 receives the set of electrical characteristics from the signal sensing circuit 110 and provides data representing the set of electrical characteristics at a harmonic frequency associated with the signal sampled by the signal sensing circuit 110 to a digital signal processing (DSP) circuit 130.

The DSP circuit 130 determines information about the load, such as load impedance, power dissipation, discharge current from the load, etc., based on the data received from the ASP circuit 120. In the described embodiment, the DSP circuit 130 controls the ASP circuit 120 to select from any number of harmonic frequencies associated with the signal present on the transmission line 140. The DSP circuit 130 can be coupled to a display, a computer system, a user input device (e.g., a keyboard, mouse, etc.), and/or any number of interface devices to select, control, and/or output information about the load at each of a set of harmonic frequencies.

For example, in one embodiment, the DSP circuit 130 couples the system 100 to a computer system, a selective frequency spectrum analyzer, a display, and at least one user input device, such as a keyboard. In this embodiment, voltage, statistical amplitude variations of load current, phase, load impedance, and power dissipation at a set of harmonic frequencies are displayed. Additionally, a frequency spectrum is displayed, and impedance at a set of harmonic frequencies is plotted and displayed on a Smith chart. Furthermore, in one embodiment of the invention, a user can select, for example, a particular harmonic frequency at which to take measurements, a particular bandwidth to use in filtering the selected harmonic frequency, as well as various display options.

Figure 2:
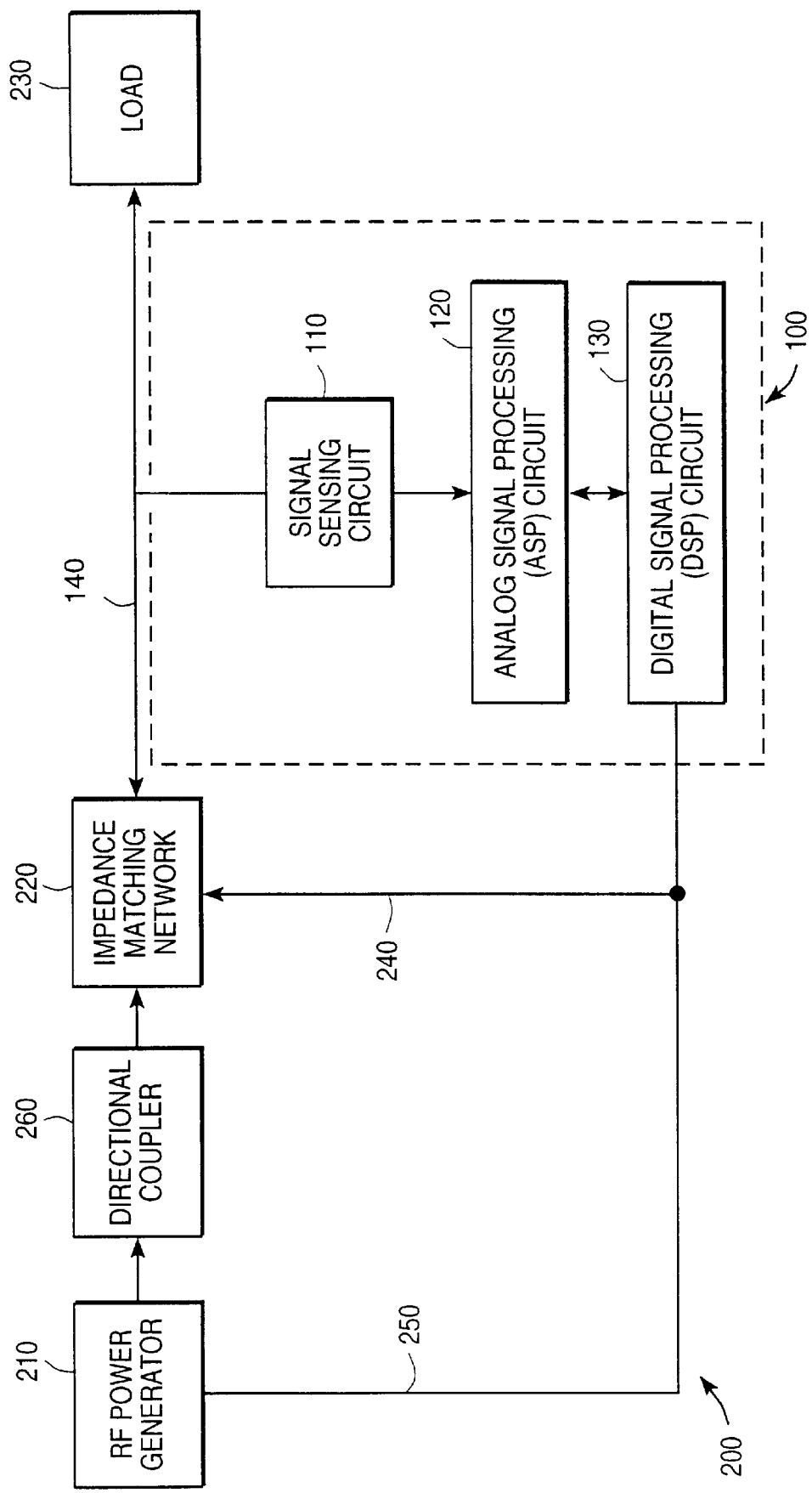
FIG. 2 is a block diagram of a system in which one embodiment of the invention can be utilized.

FIG. 2 is a block diagram of a system in which one embodiment of the invention can be utilized. In FIG. 2, a system 200 includes a radio frequency (RF) generator 210 which is used to power a load 230. The load 230 can be any number of devices (e.g., a plasma chamber). The RF generator 210 can provide a fixed or variable/selectable frequency signal to the load 230. For example, in an embodiment wherein the load 230 is a plasma chamber, the RF generator 210 provides power to the load 230 at approximately 13.56 MHz or any other frequency.

Coupled between the RF generator 210 and the load 230 are a directional coupler 260 and an impedance matching network 220. The impedance matching network 220 can be implemented in any number of ways, and is used in the system 200 primarily to provide maximum power transfer between the RF generator 210 and the load 230.

The system 200 also includes the system 100 described above in reference to FIG. 1. In the embodiment shown in FIG. 2, the system 100 is coupled between the impedance matching network 220 and the load 230, which are coupled via a transmission line 270. In addition to providing information about the load to a user, the system 100 is also coupled via feedback paths 240 and 250 to control the impedance matching network 220 and the RF generator 210, respectively, after determining load impedance and/or power dissipation at a set of harmonic frequencies. By doing so, the system 100 can provide the RF generator 210 and/or the impedance matching network 220 with control data that allows relatively efficient power transfer between the RF generator 210 and the load 230, even in the presence of harmonics.

It should be appreciated that the invention could be practiced in a number of alternative embodiments. For example, the system 100, and more specifically, the ASP circuit 120, can obtain voltage, current, phase, and/or power measurements of a signal between the RF generator 210 and the load 230 directly from the impedance matching network 220, thereby eliminating the need for the signal sensing circuit 110. Alternatively, the signal sensing circuit 110 can be implemented to detect as few as one electrical characteristic, such as current, while other electrical characteristics (e.g., voltage, phase, magnitude, etc.) are received by ASP circuit 120 from another source, such as the impedance matching network 220. While one embodiment has been described wherein the system 100 controls the RF generator 210 and the impedance matching network 220, in alternative embodiments of the invention, the system 100 does not necessarily control the RF generator 210 and/or the impedance matching network 220. Furthermore, alternative embodiments of the invention do not necessarily include the impedance matching network 220 and/or the directional coupler 260. It should further be appreciated that any number of additional devices could be used in conjunction with the system 200 for the input and/or output of information (e.g., keyboard, spectrum analyzer, display monitor, computer, etc.). Additionally, the invention could be practiced in any number of applications wherein data collection with consideration of harmonic frequencies is desired (e.g., plasma processing, medical processes, laser light, antenna tuning of transmitters, etc.).

Figure 3:
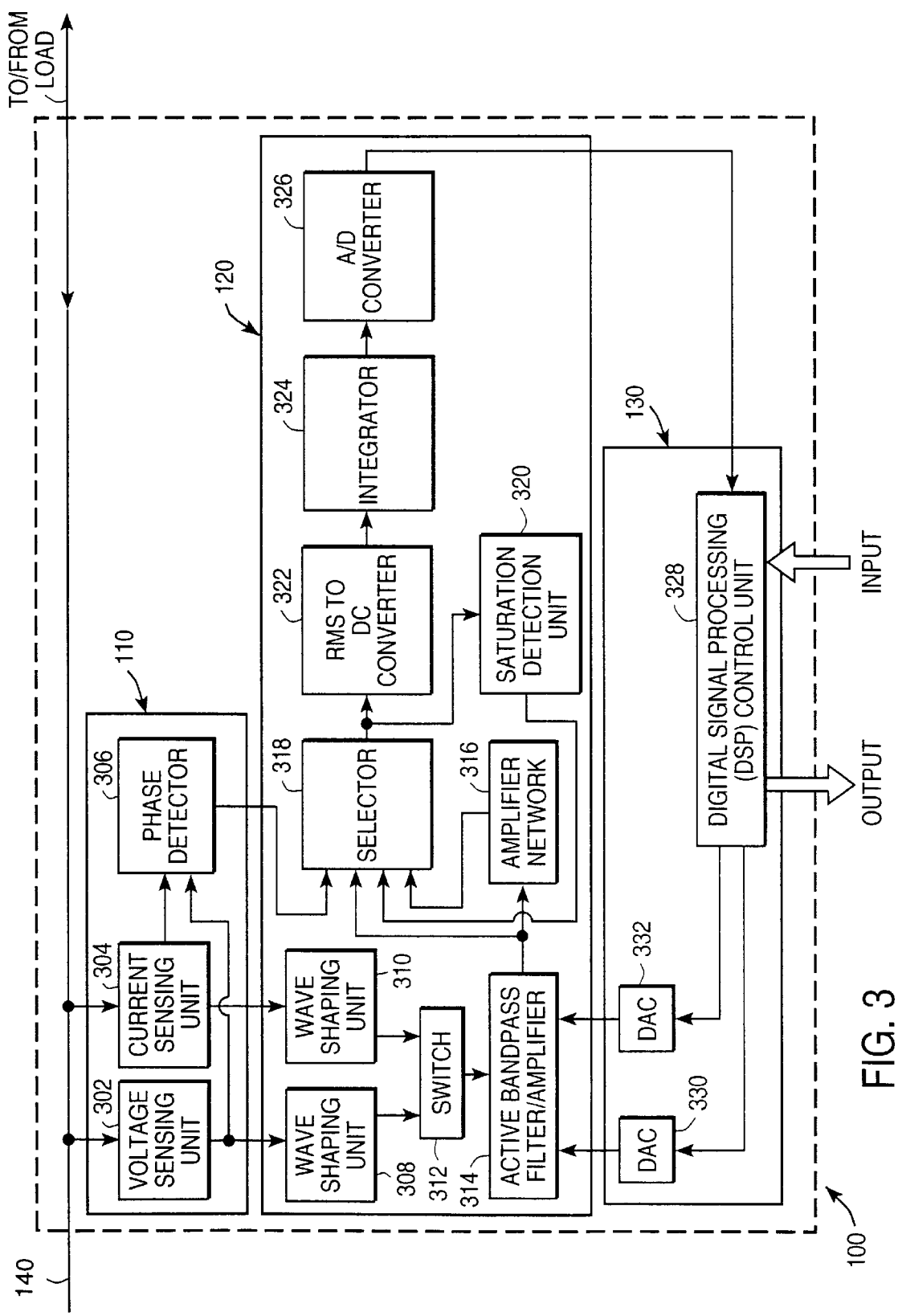
FIG. 3 is a detailed block diagram of a system according to one embodiment of the invention.

FIG. 3 is a block diagram of a system according to one embodiment of the invention. FIG. 3 illustrates a more detailed block diagram of the system 100 described in reference to FIGS. 1 and 2, which includes the signal sensing circuit 110, the analog signal processing (ASP) circuit 120, and the digital signal processing (DSP) circuit 130. The system 100 is operatively coupled to the transmission line 270. The transmission line 140 may be any number of types of medium for the transmission of an electrical signal (e.g., a metal wire, a coaxial cable, etc.). Furthermore, the transmission line may interconnect any number of types of devices, such as an impedance matching network, a load, a power source, a directional coupler, etc.

As shown in FIG. 3, the signal sensing circuit 110 comprises a voltage sensing unit 302, a current sensing unit 304, and a phase detector 306. In one embodiment, the voltage sensing unit 302 comprises a set of series capacitors for determining voltage of a signal from the transmission line 140. Similarly, the current sensing unit 304 determines current of the signal flowing to the load on the transmission line 140. In one embodiment, the current sensing unit 304 is implemented using a set of current transformers in conjunction with the transmission line 140. The phase detector 306 is used to detect any phase difference between the voltage and current detected by the voltage sensing unit 302 and the current sensing unit 304, respectively. Any number of known circuits and techniques could be used to implement the voltage sensing unit 302, the current sensing unit 304, and the phase detector 306. In alternative embodiments, the system 100 does not necessarily include the signal sensing circuit 110, or alternatively, the signal sensing circuit 110 may include any combination of a voltage sensing unit, a current sensing unit, and/or a phase detector to detect any set of electrical characteristics of the signal on the transmission line 140.

As shown in FIG. 3, the system 100 also includes the analog signal processing (ASP) circuit 120. The ASP circuit 120 includes a wave shaping unit 308 and a wave shaping unit 310, which are coupled to the voltage sensing unit 302 and the current sensing unit 304, respectively. The wave shaping unit 308 and the wave shaping unit 310 provide initial noise reduction/filtering and/or amplification of the voltage and current sampled by the voltage sensing unit 302 and the current sensing unit 304, respectively. The processed signals from the wave shaping unit 308 and the wave shaping unit 310 are coupled to a switch 312. The switch 312 selects and outputs one of the processed signals from the wave shaping unit 308 and the wave shaping unit 310 to an active bandpass filter/amplifier 314. In the described embodiment of the invention, the active bandpass filter/amplifier 314 is implemented using a set of multiplier and operational amplifier (op amp) components (e.g., Analog Devices AD834 and AD835 chips may be used).

Frequency bandwidth and corresponding Q factor for the active bandpass filter/amplifier 314 is variable and is determined by two binary DC voltage values, $V_x$ and $V_y$, such that $Q=V_y/V_x$. A digital signal processing (DSP) control unit 328 is used to determine and/or select values for the voltage $V_x$ and the voltage $V_y$, and the voltages $V_x$ and $V_y$ are provided to the active bandpass filter/amplifier 314 by the DSP control unit 328 via a digital-to-analog converter (DAC) 330 and a DAC 332, respectively.

The bandwidth (BW) for the active bandpass filter/amplifier 314 is determined using the relation BW=$k_1 \cdot V_x$, where $k_1$ is a constant that depends on an RC time constant (s) and/or reference voltage(s) for the set of multipliers in the active bandpass filter/amplifier 314. Since the voltage $V_x$ is variably controlled by the DSP control unit 328 and determines the bandwidth, the voltage $V_x$ is a bandwidth selector. While in the described embodiment the bandwidth is variably controlled/selected by the DSP control unit 328, in alternative embodiments, the bandwidth may be a fixed value.

The center frequency $f_0$ for the active bandpass filter/amplifier 314 is determined by the relationship $f_0=k_2 \cdot V_y$, where $k_2$=A/10, and A is the amplifier gain. Since the center frequency to is a function of the voltage $V_y$, which is variably controlled/selected by the DSP control unit 328, $V_y$ is a spectral frequency selector. For example, if an RF generator is delivering power to a load (e.g., a plasma chamber) at 13.56 MHz via the transmission line 140 and a particular harmonic frequency such as 27.12 MHz is selected for monitoring load parameters (e.g., load impedance, discharge current, power dissipation, etc.), the voltage $V_y$ will be selected such that $f_0$ is substantially equal to 27.12 MHz. For selecting another harmonic frequency such as 40.68 MHz, the voltage $V_y$ will be selected such that $f_0$ is substantially equal to 40.68 MHz. In one embodiment, $f_0$ is variable in the frequency range 10 MHz to 80 MHz. In alternative embodiments, $f_0$ can be variable in any number of frequency ranges or be fixed at a particular (harmonic) frequency.

Once a current and/or voltage is sampled at a particular harmonic frequency, as determined by the DSP control unit 328 and the active bandpass filter/amplifier 314, the sampled signal is provided to a switch 318 and an amplifier network 316. The amplifier network 316 is used to provide gain to the sampled signal until a desired signal level is reached. In one embodiment of the invention, the amplifier network 316 comprises 2 amplifiers. Each amplifier in the amplifier network 316 provides an amplified (sampled) signal to the selector 318. Controlling the selector 318 is a saturation detection unit 320 which compares the output of the selector 318 to a reference voltage to prevent saturation and provide at the output of the selector 318 a signal having a desired amplitude. Using the feedback control of the saturation detection unit 320, the selector 318 selects for output a signal having desired gain from the active bandpass filter/amplifier 314, or (an amplifier in) the amplifier network 316, etc.

Finally, the ASP circuit 120 includes an RMS-to-DC converter 322, an integrator 324, and an analog-to-digital (A/D) converter 326. The RMS-to-DC converter 322 accepts as its input the output of the selector 318 and converts the input to a direct current (DC) value. The integrator 324 is coupled to accept as its input the DC signal provided by the output of the RMS-to-DC converter 322, and determine an average value for sampled values of voltage and/or current over a predetermined period of time. The A/D converter 326, which is coupled to accept as its input the output of the integrator 324, converts a value determined by the integrator 324 into a binary value. In one embodiment, the A/D converter 326 outputs an 8 bit binary value.

The DSP circuit 130, which accepts the output of the A/D converter 326, includes the DSP control unit 328, the DAC 330 and the DAC 332. The DSP control unit 328 accepts a binary value representing sampled current and/or voltage from the A/D converter 326. As described above, the DAC 330 and DAC 332 provide the bandwidth selector voltage $V_x$ and the spectral frequency selector voltage $V_y$, respectively, to the active bandpass filter/amplifier 314. The DSP control unit 328 controls the bandwidth selector voltage $V_x$ and the spectral frequency selector voltage $V_y$. Thus, information about the load (e.g., load impedance) could be determined at a selected harmonic frequency (and/or fundamental frequency) based on the current and/or voltage detected and measured at the selected harmonic frequency.

As shown in FIG. 2, the system 100 can be utilized in conjunction with a directional coupler for measuring incident power $P_I$ and/or reflected power $P_R$. In such an embodiment, the reflection coefficient ρ from the directional coupler, which can be calculated using the relationship $\rho^2=P_R/P_I$, is used to determine the load impedance $Z_L$ using the relationship:

$$Z_L = \frac{1+\rho}{1-\rho}Z_0.$$

where $Z_0$ is impedance at a reference frequency (e.g., a fundamental frequency), $P_R$ is reflected power, and $P_I$ is incident/forward power.

Using the phase detector 306 and a magnitude obtained from the voltage sensing unit 302, the phase and amplitude of the power signal (e.g., at the input of the matching network 220) can be determined at each of a set of harmonic frequencies. Furthermore, since power is a scalar quantity, total power for a set of harmonic frequencies (e.g., first, second, third, fourth, fifth . . . harmonic) can be determined by summing power determined for each harmonic in the set of harmonic frequencies.

In one embodiment of the invention, the DSP control unit 328 is coupled to a computer system, a user input device (e.g., keyboard, mouse, etc.) and a display (e.g., CRT monitor). In this embodiment, load impedance for each of a set of harmonics and/or the sum of a set of harmonics is provided to a user on a Smith chart. Additionally, voltage, current, and phase at each of a set of harmonics are displayed. Statistical data for stray current from the load is also displayed.

Information about the load provided by the system 100 can be used in any number of ways. For example, in an embodiment wherein the load is an RF powered plasma chamber, the invention allows a user to take an "electronic signature" corresponding to particular plasma conditions (e.g., vacuum pressure, deposition species, RF power level, etc.) by displaying and/or storing parameters of the plasma chamber (e.g., discharge current, impedance, power dissipation, etc.) at various harmonic frequencies relative to the fundamental frequency (typically, 13.56 MHz) of the RF signal used to power the plasma chamber. To obtain/repeat a desired status of the plasma chamber, system variables (e.g., RF power level, plasma chemistry, etc.) can be adjusted to match the plasma chamber parameters (e.g., impedance, discharge current, etc.) to the previously recorded electronic signature corresponding to the desired state of the plasma chamber. Furthermore, as described above with reference to FIG. 2, information about the load at various harmonic frequencies can be provided to an impedance matching network (and/or the power source) that may be used in conjunction with the system 100 to provide maximum power transfer to the load.

It should be appreciated that the invention could be used in any number of RF powered systems, and thus, the invention should not be limited to plasma processing applications. For example, the invention could be implemented in medical applications, food tempering and thawing, ceramic heating systems comprising a laser, transmission antennas, etc.

ALTERNATIVE EMBODIMENTS

While the invention has been described in terms of several embodiments, those skilled in the art will recognize that the invention is not limited to the embodiments described. The method and apparatus of the invention can be practiced with modification and alteration within the spirit and scope of the appended claims. The description is thus to be regarded as illustrative instead of limiting on the invention.

What is claimed is:

1. An apparatus that provides information about a load, said load being operatively coupled to a power source via a transmission medium, said apparatus comprising:

a signal sensing circuit coupled to said transmission medium that detects a characteristic of a signal transmitted between said power source and said load via said transmission medium;

an analog signal processing (ASP) circuit, coupled to said signal sensing circuit to provide data representing said characteristic at a harmonic frequency associated with said signal; and a digital signal processing (DSP) circuit coupled to said ASP circuit to receive said data and to control selection of the harmonic frequency, said DSP circuit determining said information based on said data.

2. The apparatus of claim 1, wherein said load is a plasma processing chamber.

3. The apparatus of claim 2, wherein said power source is a radio frequency (RF) power generator.

4. The apparatus of claim 1, wherein said ASP circuit is controlled by said DSP circuit to select said harmonic frequency from a set of harmonic frequencies.

5. The apparatus of claim 1, wherein said information comprises load impedance.

6. The apparatus of claim 1, wherein said information comprises power delivered to said load.

7. The apparatus of claim 1, further comprising an impedance matching network coupled between said power source and said load via said transmission medium, said impedance matching network operatively coupled to receive said data to match impedance of said load with said source.

8. The apparatus of claim 1, further comprising:

a user interface coupled to said DSP circuit, said user interface allowing selection of a type of said information; and a display coupled to said user interface to display said information.

9. The apparatus of claim 1, wherein said ASP circuit comprises a bandpass filter having a center frequency substantially equal to said harmonic frequency.

10. The apparatus of claim 9, wherein said center frequency is selectable.

11. The apparatus of claim 10, wherein selection of said center frequency is controlled by said DSP circuit.

12. The apparatus of claim 9, wherein a bandwidth of said bandpass filter is selectable.

13. The apparatus of claim 12, wherein selection of said bandwidth is controlled by said DSP circuit.

14. The apparatus of claim 1, wherein said signal sensing circuit comprises:

a voltage and magnitude sensor;

a current sensor; and a phase detector.

15. The apparatus of claim 1 further comprising a directional coupler coupled to said ASP signal sensing circuit via said transmission medium to allow detection of said characteristic when said signal is reflected from said load and when said signal is incident to said load.

16. An apparatus for use with a power source and a load, said apparatus comprising:

a detection means for detecting a characteristic of a signal transmitted over a transmission medium coupled between said power source and said load;

an analog signal processing (ASP) means for providing data representing said characteristic at a harmonic frequency associated with said signal; and a digital signal processing (DSP) means for controlling selecting the harmonic frequency and determining information about said load based on receiving said data.

17. In a radio frequency (RF) powered system comprising an RF power source and a load, an apparatus for determining information about said load at a harmonic frequency associated with a signal present transmitted via a transmission medium coupled between said RF power source and said load, said apparatus comprising:

an analog signal processing (ASP) circuit comprising:

a filter that provides a characteristic of said signal at said harmonic frequency;

an analog-to-digital (A/D) converter coupled to said filter, said A/D converter generating data representing said characteristic of said signal at said harmonic frequency; and a digital signal processing (DSP) circuit coupled to said ASP circuit to control selecting said harmonic frequency and receive said data, said DSP circuit determining said information based on said data.

18. The RF powered system of claim 17, further comprising an impedance matching network, said impedance matching network being coupled to said DSP circuit to receive control data representing said information to use in controlling power delivery to said load.

19. The apparatus of claim 17, wherein said load is a plasma chamber.

20. The apparatus of claim 17, further comprising:

a voltage sensor coupled to said ASP circuit, said voltage sensor providing voltage associated with said signal to said ASP circuit.

21. The apparatus of claim 20, further comprising:

a current sensor coupled to said ASP circuit, said current sensor providing current associated with said signal to said ASP circuit.

22. The apparatus of claim 21, further comprising a phase detector that determines a phase difference between said current and said voltage.

23. The apparatus of claim 17, further comprising a directional coupler for determining the direction of said signal relative to said load, said signal being a power signal.

24. The apparatus of claim 17, wherein said information comprises impedance of said load at said harmonic frequency.

25. The apparatus of claim 17, further comprising an impedance matching network coupled between said RF power source and said load via said transmission medium, said impedance matching network providing an electrical characteristic of said signal to said ASP circuit.

* * * * *

UNITED STATES PATENT AND TRADEMARK OFFICE
CERTIFICATE OF CORRECTION

PATENT NO. : 6,046,594  
DATED : April 4, 2000  
INVENTOR(S) : Mavretic

Page 1 of 1

It is certified that error appears in the above-identified patent and that said Letters Patent is hereby corrected as shown below:

Column 4,
Line 50, delete "270" and insert -- 140 --.

Column 5,
Line 52, delete "to" insert -- $F_o$ --.

Signed and Sealed this

Twenty-fifth Day of December, 2001

Attest:

JAMES E. ROGAN
*Attesting Officer*   *Director of the United States Patent and Trademark Office*